United States Patent [19]

Rucheton et al.

[11] Patent Number: 5,650,269
[45] Date of Patent: Jul. 22, 1997

[54] METHOD FOR DETECTING VIRAL COMPOUNDS USING A β2'-GLYCOPROTEIN I

[76] Inventors: Marcel Rucheton, 10, rue de la Confrérie, 34000 Montpellier; Elie Stefas, 94, Allée des Fauvettes, 34280 La Grande-Motte; Hubert Graafland, 10 A, Avenue du Professeur Grasset, 34000 Montpellier, all of France

[21] Appl. No.: 500,956
[22] PCT Filed: Feb. 9, 1994
[86] PCT No.: PCT/FR94/00142
  § 371 Date: Aug. 10, 1995
  § 102(e) Date: Aug. 10, 1995
[87] PCT Pub. No.: WO94/18569
  PCT Pub. Date: Aug. 18, 1994

[30] Foreign Application Priority Data

Feb. 9, 1993 [FR] France .................................. 93 01400

[51] Int. Cl.$^6$ .............................. C12Q 1/70; G01N 33/53; G01N 33/543; C07K 14/00
[52] U.S. Cl. .............................. 435/5; 435/7.1; 435/7.92; 436/518; 436/531; 530/350; 530/395
[58] Field of Search ................................ 435/5, 7.1, 7.92; 436/518, 531; 530/350, 395

[56] References Cited

FOREIGN PATENT DOCUMENTS 0124896  11/1984  European Pat. Off. .

*Primary Examiner*—Marian C. Knode
*Assistant Examiner*—Henry E. Auer
*Attorney, Agent, or Firm*—Cushman Darby & Cushman Intellectual Property Group of Pillsbury Madison & Sutro LLP

[57] ABSTRACT

A method for detecting and/or assaying viral compounds, wherein the viral compounds are bound with β2'-glycoprotein I which is a glycoprotein having a molecular weight of 50,000±3,000 daltons from the method for producing albumin obtained as a blood plasma by-product according to FR-A 2 690 444. Viral compound separation may be simplified by binding the β2'-glycoprotein I to a preferably solid support or by binding the viral compounds to a support and exposing same with the β2'-glycoprotein I conjugated with a marker. A solid support to which at least the β2'-glycoprotein I is bound, is also disclosed.

25 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
         Gly Arg Thr Cys Pro Lys Pro Asp Asp Leu Pro Phe Ser Thr Val Val
         1               5                   10                  15
         Pro Leu Lys Thr
                     20
```

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
         Phe Trp Lys Ser Asp Ala Ser
         1               5
```

METHOD FOR DETECTING VIRAL COMPOUNDS USING A β2'-GLYCOPROTEIN I

This application is a 371 of PCT/FR94/00142 filed Feb. 9, 1994.

The present invention relates to a method for detecting and/or assaying viral compounds and to a support bearing at least one glycoprotein.

According to the present invention, the term viral compound refers both to the compounds, in particular the proteins, constituting a virus and to particles of viral type. Particles of viral type are either virions, which may be complete or incomplete, or portions of virion, or assemblies containing constituent compounds of viruses, which have certain properties of viruses or of viral compounds; in particular, they are detected by certain antibodies specific for viral compounds or may be similar to these viral compounds.

According to the present invention, it has been found that certain viral compounds bound themselves specifically to one glycoprotein: β2'-glycoprotein I or a protein composition containing β2'-glycoprotein I. β2'-Glycoprotein I is the glycoprotein described in the French patent application filed under No. 93 01399 by the same applicants on 9 Feb. 1993. β2'-Glycoprotein I binds to the membrane of viral particles, as well as to certain chemical or biological surfaces or compounds. According to the present invention, this property is used in order to uptake and isolate viral compounds, thereby allowing them to be detected and/or assayed.

The subject of the present invention is thus a method for detecting and/or assaying viral compounds, characterized in that the viral compounds are bound using β2'-glycoprotein I.

According to the invention, β2'-glycoprotein I may be used pure or in the form of a protein composition containing in particular other glycoproteins, possibly other β2'-glycoproteins. This composition may, in particular, be that obtained by elution of an affinity column on a gel bearing sulfate groups as described in French patent application 93 01399.

According to a first embodiment of the method, β2'-glycoprotein I is bound to a support, a viral compound contained in a biological fluid or extracted from a biological tissue is then bound to the β2'-glycoprotein I so as to separate the said viral compound from the compounds which are not capable of binding to β2'-glycoprotein I, and the viral compound bound to the β2'-glycoprotein I is detected and/or assayed by any method for detecting and/or assaying this vital compound.

According to a second embodiment of the method, the viral compound is bound to a support and is exposed with β2'-glycoprotein I conjugated with a label. The viral compound may be bound either directly to the support or indirectly, for example via an antibody. The label may advantageously be an enzyme or a radioactive product.

β2'-Glycoprotein I is the glycoprotein isolated from the residue bound to the affinity chromatography column(s) used in the method for the purification of albumin from blood plasma, described in FR-A 2,690,444. According to this document, the albumin is separated from the other proteins by a liquid phase chromatographic method in which the aqueous solution containing the albumin is passed through at least one so-called "hydrophobic" chromatography column filled with a particulate material capable of retaining some of the proteins other than albumin; in order to complete the separation, it is also proposed to pass the aqueous albumin solution through at least one affinity chromatography column containing a neutral particulate support or a particulate support which is close to neutrality charged with a polysulfated compound. The effluent obtained by this method consists of a solution of purified albumin, the majority of the proteins other than the albumin being bound either to the hydrophobic chromatography column(s) or to the affinity chromatography column(s).

This method is carried out, for example, as follows:

A raw aqueous solution of albumin is preferably obtained from blood plasma, in particular human plasma, by a known process of COHN type, according to which the plasma is fractionated by successive treatments by modifying the temperature and by the action of the precipitation agent in order to obtain, after at least partial separation of the factors VIII and IX and of the γ-globulins, albumin solutions in order to extract the precipitation agent and to collect the raw albumin solution.

The raw aqueous solution of albumin advantageously has a raw albumin concentration of between 1 g and 300 g per liter and has a pH between 6 and 8, preferably between 6.9 and 7.1. The compound containing $C_3$ to $C_8$ alkyl radicals with which the stationary phase is charged is preferably a butyl radical. The packing bed of the chromatography column(s) then consists, in particular, of the product marketed by MERCK under the tradename "FRACTOGEL TSK-BUTYL-650".

The compound containing sulfate groups with which the stationary phase is charged is preferably a dextran sulfate. The packing bed of the chromatography column(s) consists, in particular, of the product marketed under the tradename "DEXTRAN BEADS SULFATED" by SIGMA.

The raw aqueous solution of albumin is preferably subjected to at least two chromatographies, at least one being a chromatography on a stationary phase charged with a compound containing $C_3$ to $C_8$ alkyl radicals and at least one other being a chromatography on a stationary phase charged with a compound containing sulfate groups.

The chromatography temperature is from 1° to 30° C. The column chromatography flow rate is generally between 1 and 30 cm/hour.

Before subjecting an aqueous albumin solution to a chromatography on a stationary phase charged with a compound bearing sulfate groups, the corresponding column(s) is (are) equilibrated with a saline solution which is at most isotonic relative to the albumin solution. A sodium chloride solution or phosphate-buffered saline (PBS) is preferably used to equilibrate the chromatography column(s).

Elution is preferably carried out by increasing ionic strength through the introduction of a saline solution. The saline solution is preferably a solution of NaCl in a concentration of at least 0.3M., and advantageously, of 2M. It is advantageously preceded by a washing operation. The affinity chromatography medium is washed using a saline buffer having a molarity of 0.16 mole/liter, preferably a phosphated buffer composed of mono- and disodium phosphates, in particular at a molarity of 0.01 mole/liter, and of sodium chloride, in particular in a molarity of 0.15 mole/liter, in proportions giving a pH of 7.00±0.05. The washing operation is continued until the optical density of the effluent becomes greater than a predetermined value, e.g. 0.1 UOD (Unit of Optical Density).

By subjecting the support of the above-mentioned affinity chromatography column(s) to an elution, preferably to an elution by increasing the ionic strength, a protein composition is obtained in which the protein content contains from 5 to 100% by weight of β2'-glycoprotein I.

β2'-Glycoprotein I has a molecular weight of 50,000±3,000 daltons, and the first 20 amino acids of the N-terminal region of β2'-glycoprotein I are as follows: Gly-Arg-Thr-Cys-Pro-Lys-Pro-Asp-Asp-Leu-Pro-Phe-Ser-Thr-Val-Val-Pro-Leu-Lys-Thr (SEQ ID No:1) and the sequence of amino acids 315 to 321 is Phe-Trp-Lys-Ser-Asp-Ala-Ser (SEQ ID NO:2).

The viral compounds capable of being recognized by β2'-glycoprotein I may more particularly originate from the following viruses: preferably hepatitis B virus (HBV), human immunodeficiency virus ($HIV_1$ and $HIV_2$) and equally simian immunodeficiency virus (SIV) or herpes simplex virus (HSV) or may be particles or proteins of viral origin, or similar to these, which are present in certain leukemias or myelomas or in Gougerot-Sjögren syndrome.

According to the first embodiment of the method according to the invention, β2'-glycoprotein I is first bound to a support. It should be noted that when a protein composition containing β2'-glycoprotein I and other glycoproteins is used, these other glycoproteins may also bind to the support. A solid support is preferably used, more particularly one consisting of a titration microplate, for example an ELISA microplate.

Binding of β2'-glycoprotein I (and possibly of other glycoproteins) to the support takes place by reaction of reactive groups of the glycoprotein with reactive sites of the support. This reaction is preferably carried out at a temperature of 0° to 40° C., the β2'-glycoprotein I preferably being placed in a buffer having a pH between 4.5 and 10.5, preferably between 5.5 and 6.5. The buffer may be of the phosphate or acetate type. The solution obtained advantageously has a concentration between 0.01 to 100 mg/l of β2'-glycoprotein I. The support is advantageously kept in contact with the buffer containing the β2'-glycoprotein I at a temperature of 0° to 40° C. and for an incubation time other glycoproteins). In this case, other active groups are reacted with these active sites. With this aim, a bovine serum albumin solution or casein solution, in particular 2% solution in the buffer used for the β2'-glycoprotein I, is advantageously used. After reaction, the support is also preferably rinsed and dried.

The rinsed and dried support on which at least the β2'-glycoprotein is bound may be stored before binding the viral compounds. This storage is preferably effected at +4° C. or -20° C.

The support on which at least the β2'-glycoprotein I (and possibly other glycoproteins) is bound is then placed in contact with a biological fluid liable to contain viral compounds. This fluid is either prepared from organs or biological liquids of a patient suffering from a viral pathology, or is derived from supernatants of "in vitro" viral cultures. The biological liquid may be a serum, urine, cephalorrachidian fluid, synovial fluid, peritoneal fluid, pleural fluid, seminal fluid or ascitic fluid. A blood plasma or serum is preferably used. The biological fluid is preferably diluted using a buffer giving a pH between 4.5 and 10, advantageously 5.6. The reaction is preferably carried out at a temperature of 0° C. to 42° C., advantageously in the region of 37° C., for a period of 30 minutes to 24 hours. The biological fluid and the support bearing the β2'-glycoprotein I (and possibly other glycoproteins), which may have bound a viral compound, are then separated. A washing operation is then optionally carried out, with a solution which is preferably buffered.

Detection and/or assaying of the viral compound bound to the β2'-glycoprotein I may be performed by any known means, such as the infectivity or the detection of specific nucleic acids by the so-called "Polymerase Chain Reaction (PCR)" technique. This technique is described, for example, in the article by Mullis K. B. and Faloona F. A. in Methods Enzymol. 1987 155 pages 335–350. The detection and/or assaying are preferably performed using an antibody which specifically recognizes proteins of the viral compounds to be detected. In a known manner, this antibody may be conjugated with an enzymatic label, for example peroxidase. The excess antibody is removed by washing. A substrate specific for the enzyme conjugated with the antibody is then added in a known manner, and under specific conditions this substrate is converted into a colored product. Formation of the said colored Reaction (PCR)" technique. This technique is described, for example, in the article by Mullis K. B. and Faloona F. A. in Methods Enzymol. 1987 155 pages 335–350. The detection and/or assaying are preferably performed using an antibody which specifically recognizes proteins of the vital compounds to be detected. In a known manner, this antibody may be conjugated with an enzymatic label, for example peroxidase. The excess antibody is removed by washing. A substrate specific for the enzyme conjugated with the antibody is then added in a known manner, and under specific conditions this substrate is converted into a colored product. Formation of the said colored compound indicates the presence of the desired viral compound and allows this viral compound to be assayed.

According to the second embodiment of the method according to the invention, the viral compound is bound to a solid support which may be a membrane, for example a nitrocellulose membrane, or a titration microplate, for example an ELISA microplate.

The viral compound is bound to the support by reaction of reactive groups of the vital compound with the reactive sites of the support when the binding is direct, or by binding of a compound, for example an antibody, to the reactive sites of the support and binding of the viral compound to the said compound bound to the support. This reaction is preferably carried out at a temperature of 0° to 40° C., the viral compound preferably being placed in a buffer having a pH between 4.5 and 10.5, preferably between 6.5 and 7.5. The buffer may be of the phosphate or acetate type. The support is advantageously kept in contact with the buffer containing the viral compound at a temperature of 0° to 40° C. and for an incubation time of between 30 minutes and 24 hours.

After incubation, the buffer containing the unreacted viral compound is separated from the support and the support is washed, preferably with the same buffer as that which contained the viral compound. It may be necessary to saturate the active sites of the support which have not reacted with the viral compound. In this case, other active groups are reacted with these active sites. With this aim, a bovine serum albumin solution or casein solution is advantageously used. After reaction, the support is also preferably rinsed and dried.

The support on which the viral compound is bound is then placed in contact with a solution of β2'-glycoprotein I conjugated with a label. The solution containing the β2'-glycoprotein I is preferably diluted using a buffer giving a pH between 4.5 and 10, advantageously 5.6. The reaction is preferably carried out at a temperature of 0° C. to 42° C., advantageously in the region of 37° C., for a period of 30 minutes to 24 hours. The solution containing the unreacted β2'-glycoprotein I is then separated from the support bearing the viral compound which may have bound the β2'-glycoprotein I. A washing operation is then optionally carried out with a solution which is preferably buffered.

Detection and/or assaying of the viral compound recognized by β2'-glycoprotein I is carried out by adding a substrate which is specific for the label conjugated with the β2'-glycoprotein I when the label is an enzyme, or by measuring the radioactivity when the label is radioactive.

The examples below, given purely by way of illustration and with no limitation being implied, will allow a better understanding of the invention to be gained.

EXAMPLE 1

Detection of the hepatitis B virus

A) Binding of β2'-glycoprotein I to a support

The support used is a microtitration plate of micro-ELISA type with 96 flat-bottomed wells, marketed by the company "Dynatech". A β2'-glycoprotein I solution having a concentration of 10 micrograms/ml (μg/ml) is prepared in an acetate buffer containing 0.05 mol/l of acetic acid and of acetate and having a pH of 5.6±0.05.

100 μl of this solution are placed at the bottom of each well of the microplate. The latter is then incubated at +4° C. for 18 hours. The liquid of each well is then drawn off with suction. 300 to 400 μl of phosphate buffer containing 0.01 mol/l of monosodium and disodium phosphate and 0.15 mol/l of sodium chloride and having a pH of 7.00±0.05 are then introduced into each well. This buffer is left in contact with the support for 3 minutes and is then drawn off with suction; this washing operation is carried out 3 times.

In order to saturate the microplate sites which may still be active, 200 μl of a bovine albumin solution at a concentration of 2% by weight in the phosphate buffer described Move are placed in each well. The microplate is then incubated at 37° C. for 90 minutes. The solution contained in each well is then drawn off with suction. A washing operation is then carried out by introducing 300 to 400 μl of phosphate buffer per well, followed by leaving the solution in contact for 3 minutes, and finally by drawing off the solution with suction; this washing operation is repeated 5 times. The plate is then dried.

The plate on which the β2'-glycoprotein I is bound is then stored at +4° C. or at −20° C.

B) Binding of vital compounds 48 samples of blood serum from patients suffering from viral hepatitis B containing the antigen of the virus HBV (AgHB$_g$) and, by way of comparison, 48 samples of blood serum from healthy donors were used. Each serum sample is diluted 100 times. The dilution is carried out using a buffer (acetic acid/sodium acetate) having an acetate and acetic acid concentration of 0.05 mol/l and a pH of 5.6±0.05. 100 μl of solution are placed at the bottom of each well of the plate which is prepared and stored according to A. The plate is incubated at +37° C. for a period of 90 minutes. After this incubation, a washing operation is carried out by introducing 300 μl of phosphate buffer into each well, the mixture is left in contact for 2 minutes and the buffer solution is drawn off with suction; this washing operation is repeated 3 times.

C) Detection of viral compounds

100 μl of a solution of monoclonal antibody which is specific against AgHB$_s$ of the hepatitis B virus conjugated with peroxidase are added per well. The plate is left to incubate at 37° C. for 60 minutes. After this incubation, the content of the wells of the plate is drawn off with suction. 300 μl of phosphate buffer are introduced into each well and, after a contact time of 2 minutes, the buffer is drawn off with suction: this washing operation is repeated 3 times.

100 μl of o-phenylenediamine.2HCl solution in sodium citrate buffer are added per well. The mixture is left to incubate for 30 minutes at room temperature and the reaction is then stopped by adding 50 μl of 2N H$_2$SO$_4$ to each well. The absorbance at 492 nm obtained after the reaction is measured using a plate reader robot.

The average of the absorbances obtained for each patient or donor are given in Table I as ODU×100. Samples A1 to D12 correspond to the 48 sera from sick patients and samples E1 to H12 correspond to the donor sera.

These results show that by the test according to the present application:

1) all the sera from healthy donors have effectively been recognized as negative, 2) 77.1% of the sera from sick patients have been recognized as positive and only 22.9% as negative.

TABLE I

|   | 1 | 2 | 3 | 4 | 5 | 6 | 7 | 8 | 9 | 10 | 11 | 12 |
|---|---|---|---|---|---|---|---|---|---|----|----|----|
| A | 136 | 2500 | 71 | 1565 | 1993 | 304 | 50 | 82 | 2420 | 843 | 2500 | 48 |
| B | 42 | 230 | 95 | 157 | 95 | 65 | 850 | 1180 | 2485 | 56 | 89 | 555 |
| C | 44 | 59 | 51 | 115 | 1521 | 68 | 1016 | 44 | 171 | 57 | 58 | 1140 |
| D | 2489 | 2510 | 2498 | 114 | 658 | 2500 | 1289 | 1979 | 2495 | 48 | 911 | 1560 |
| E | 46 | 54 | 47 | 42 | 47 | 50 | 45 | 44 | 51 | 53 | 47 | 43 |
| F | 49 | 49 | 49 | 46 | 54 | 57 | 47 | 46 | 54 | 51 | 49 | 48 |
| G | 54 | 54 | 52 | 42 | 47 | 50 | 45 | 44 | 53 | 48 | 50 | 47 |
| H | 54 | 51 | 50 | 49 | 52 | 52 | 51 | 45 | 48 | 52 | 49 | 51 |

EXAMPLE 2

Detection of the HIV$_1$ virus

The support used is a microtitration plate of micro-ELISA 96-well flat-bottomed type, marketed by the company "Dynatech". A β2'-glycoprotein I solution having a concentration of 10 μg/ml is prepared in an acetate buffer containing 0.05 mol/l of acetic acid and sodium acetate and having a pH of 5.6±0.05. 100 μl of this solution are placed at the bottom of each well of the microplate. The latter is then incubated at +4° C. for 18 hours. The liquid is then drawn off with suction from each well. 300 to 400 μl of phosphate buffer containing 0.01 mol/l of monosodium and disodium phosphate and 0.15 mol/l of sodium chloride and having a pH of 7.00±0.05 are then introduced into each well. The buffer is left in contact with the support for 3 minutes and is drawn off with suction; this washing operation is carried out 3 times.

In order to saturate the microplate sites which may still be active, 200 μl of a bovine albumin solution at a concentration of 2% by weight in the phosphate buffer described above are placed in each well. The microplate is then incubated at 37° C. for 90 minutes. The solution contained in each well is then drawn off with suction. A washing operation is then carried out by introducing 300 to 400 μl of phosphate buffer per well, followed by leaving the solution in contact for 3 minutes, and finally by drawing off the solution with suction; this washing operation is repeated 5 times. The plate is then dried.

17 samples of serum from healthy donors and 17 samples of serum from patients infected with $HIV_1$ were used. The serum sample is diluted 100 times in the acetate buffer described above. 100 µl of solution are placed at the bottom of each well of the plate prepared as above. The plate is incubated at +37° C. for a period of 90 minutes. After this incubation, a washing operation is carried out by introducing 300 µl of phosphate buffer into each well, the mixture is left in contact for 2 minutes and the buffer solution is drawn off with suction; this washing operation is repeated 5 times.

100 µl of a solution of human polyclonal anti-bodies which are specific for HIV:, conjugated with peroxidase and marketed by the Institut Pasteur-SANOFI, are then added per well. The plate is left to incubate at 37° C. for 60 minutes. After this incubation, the content of the wells of the plate is drawn off with suction. 300 µl of phosphate buffer are introduced into each well and, after a contact time of 2 minutes, the buffer is drawn off with suction: this washing operation is repeated 3 times.

100 1 of o-phenylenediamine.2HCl solution in sodium citrate buffer are added per well. The mixture is left to incubate for 30 minutes at room temperature and the reaction is then stopped by adding 50 µl of 2N $H_2SO_4$ to each well. The absorbance at 492 nm obtained after the reaction is measured in ODU using a plate reader robot. The results obtained are given in Table II below:

| Samples | Healthy donors | Sick patients |
| --- | --- | --- |
| 1 | 0.088 | 0.549 |
| 2 | 0.058 | 0.544 |
| 3 | 0.074 | 2.151 |
| 4 | 0.070 | 0.892 |
| 5 | 0.071 | 2.900 |
| 6 | 0.080 | 0.121 |
| 7 | 0.070 | 0.160 |
| 8 | 0.072 | 0.134 |
| 9 | 0.081 | 0.233 |
| 10 | 0.078 | 1.330 |
| 11 | 0.070 | 0.141 |
| 12 | 0.073 | 0.093 |
| 13 | 0.075 | 0.291 |
| 14 | 0.076 | 0.644 |
| 15 | 0.082 | 0.350 |
| 16 | 0.080 | 0.550 |
| 17 | 0.083 | 0.510 |

It can be seen that for all the sera from healthy patients, the absorbance is less than 0.1;

among the sera from sick patients, 12 have an absorbance greater than 0.20 DU (i.e. 70%)

4 have an absorbance between 0.1 and 0.2 ODU (i.e. 23.5%)

(consequently, 93.5% may be considered as positive)

1 is considered as negative (6.5%), having an absorbance of less than 0.1.

EXAMPLE 3

Various amounts, 300 ng, 30 ng, 3 ng and 0 ng, of recombinant protein p26-$HIV_2$ ROD in solution in an aqueous mixture of ethanolamine (12 g/l) and glycine (24 g/l) are filtered through a nitrocellulose membrane (BA 83, Schleicher and Schuell), by suction of a few $mm^3$ (1 to 3) in different areas, so as to retain on the membrane at least some of the recombinant protein. The membrane is then saturated by incubation in the presence of 1% by weight of polyvinylpyrrolidone having a molecular weight in the region of 10,000 kdaltons in solution in the same ethanolamine and glycine mixture as above. The mixture is then rinsed with a buffer solution containing 5 mMol of $NaH_2PO_4$, 5 mM of $Na_2HPO_4$, 125 mM of NaCl and 0.05% by weight of "TWEEN 20".

About 40 ng of β2'-glycoprotein I coupled with alkaline phosphatase in solution in 200 µl of the phosphate buffer described above are reacted with the membrane for 1 hour at 37° C. The mixture is then rinsed 3 times with the ethanolamine and glycine solution above. The alkaline phosphatase activity is exposed in the presence of nitro-blue-tetrazolium (NBT) and 4-bromo-4-chloro-3-indolyl phosphate (BCIP) in a solution containing 50 mM of tris (hydroxymethyl)aminomethane at pH 8 and 0.1M of NaCl. It can be seen on the membrane that β2'-glycoprotein I makes it possible to expose the presence of the recombined protein p26-$HIV_2$ on the areas in which it is present, the membrane being more or less colored in these areas. The control area is not modified.

Under the same conditions, there is no reaction with the alkaline phosphatase alone.

EXAMPLE 4

Under identical conditions to those of Example 3, except that the incubation was carried out in the presence of fetal calf serum diluted 2,000 times instead of polyvinylpyrrolidone, a reaction with the recombinant protein gp 160-$HIV_1$, LAI was observed on the areas of the membrane impregnated with recombinant protein.

We claim:

1. A method for detecting the presence and/or amount of a viral compound in a sample, comprising the steps of
   (i) contacting the sample with β2'-glycoprotein I so that said viral compound becomes bound to β2'-glycoprotein I to form a complex; and
   (ii) detecting the presence and/or amount of said complex.

2. The method according to claim 1, wherein β2'-glycoprotein I is used in pure form or in the form of a protein composition mixed with other glycoproteins.

3. The method according to claim 1, wherein a vital compound contained in a biological fluid or extracted from a biological tissue is bound to the β2'-glycoprotein I so as to separate the said viral compound from the compounds which are not capable of binding to β2'-glycoprotein I.

4. The method according to claim 3 wherein the biological fluid is a serum, a plasma, urine, cerebrospinal fluid, synovial fluid, peritoneal fluid, pleural fluid, seminal fluid, ascitic fluid or supernatant from in vitro viral culture or a cell extract.

5. The method according to claim 3, wherein the biological fluid is diluted with a buffer having a pH between 4.5 and 10.0.

6. The method according to claim 3, wherein the binding of the viral compound is carried out at a temperature between 0° and 42° C., for a period of 30 minutes to 24 hours.

7. The method according to claim 1 wherein the viral compound is bound to a support and is contacted with β2'-glycoprotein I conjugated with a label.

8. The method according to claim 7, wherein the support, on which at least the β2'-glycoprotein I is bound, is stored.

9. The method according to claim 7, wherein the viral compound bound to the support is detected with an antibody.

10. The method according to claim 9, wherein the antibody is conjugated with an enzymatic label.

11. The method according to claim 10, wherein a substrate which is specific for the enzyme conjugated with the antibody is added.

12. The method according to claim 1 wherein the vrtal compound bound by β2'-glycoprotein I originates from hepatitis virus (HBV) or from human immunodeficiency virus ($HIV_1$ and $HIV_2$).

13. The method according to claim 1 wherein the vital compound bound by β2'-glycoprotein I originates from simian immunodeficiency virus (SIV) or from herpes simplex virus (HSV).

14. The method according to claim 1 wherein the viral compound bound by β2'-glycoprotein I is a protein or a viral particle, which is present in leukemia, myeloma or Gougerot.Sjögren syndrome.

15. The method according to claim 1 wherein the β2'-glycoprotein I or the viral compound is bound to a solid support.

16. The method according to claim 15, wherein the solid support is an ELISA microplate.

17. The method according to claim 15 wherein the β2'-glycoprotein I is dissolved is a buffer having a pH between 4.5 and 10.5 before being bound to the solid support.

18. The method according to claim 17, wherein the buffer is a phosphate or acetate buffer.

19. The method according to claim 17, wherein the β2'-glycoprotein I is at a concentration between 0.01 and 100 mg/l in the buffer.

20. The method according to claim 17, wherein the β2'-glycoprotein I is bound to the support by placing the buffer containing the β2'-glycoprotein I in contact with the support at a temperature of 0° to 40° C. for an incubation time of between 30 minutes and 24 hours.

21. The method according to claim 17, wherein the unbound β2'-glycoprotein I is separated from said support and the support is washed.

22. The method according to claim 21, wherein the support is washed with the same buffer as that used to dissolve the β2'-glycoprotein I.

23. The method according to claim 22, wherein after binding the β2'-glycoprotein I, the sites of the support which have not reacted with the β2'-glycoprotein I are blocked.

24. The method according to claim 23, wherein the sites are blocked with a bovine serum albumin solution or casein solution.

25. The method according to claim 15, wherein after the viral binding, the biological fluid is separated from the support and said support is washed.

* * * * *